(12) United States Patent
Deal

(10) Patent No.: US 8,636,651 B2
(45) Date of Patent: Jan. 28, 2014

(54) MEDICAL IMMOBILIZATION DEVICE AND RELATED METHODS OF USE

(75) Inventors: Travis Deal, Freedom, IN (US); Nancy Deal, legal representative, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 335 days.

(21) Appl. No.: 13/030,234

(22) Filed: Feb. 18, 2011

(65) Prior Publication Data

US 2011/0224489 A1 Sep. 15, 2011

Related U.S. Application Data

(60) Provisional application No. 61/313,040, filed on Mar. 11, 2010.

(51) Int. Cl.
*A61B 1/00* (2006.01)
*A61B 1/04* (2006.01)
*A61B 1/12* (2006.01)
*A61M 29/00* (2006.01)

(52) U.S. Cl.
USPC ............ 600/116; 600/115; 600/158; 604/103

(58) Field of Classification Search
USPC ......... 600/115–116, 124, 127, 153, 156, 158; 604/101–101.04, 103, 103.07
See application file for complete search history.

(56) References Cited

U.S. PATENT DOCUMENTS

| 4,202,346 | A | 5/1980 | Granier |
| 4,295,464 | A | 10/1981 | Shihata |
| 4,987,884 | A * | 1/1991 | Nishioka et al. ............... 600/181 |
| 5,833,650 | A * | 11/1998 | Imran ............................ 604/509 |
| 7,637,905 | B2 * | 12/2009 | Saadat et al. ...................... 606/1 |
| 2008/0188866 | A1 | 8/2008 | Karpiel et al. |

FOREIGN PATENT DOCUMENTS

| EP | 0 184 314 A1 | 6/1986 |
| WO | WO 01/05311 A1 | 1/2001 |
| WO | WO 01/72209 A1 | 10/2001 |

OTHER PUBLICATIONS

International Search Report and Written Opinion issued in PCT International Application No. PCT/US2011/025371 (14 pages).

* cited by examiner

*Primary Examiner* — Alireza Nia
(74) *Attorney, Agent, or Firm* — Bookoff McAndrews, PLLC

(57) ABSTRACT

Embodiments of the invention are directed to a medical device and methods of immobilizing and retrieving material from a body. The medical device, in an embodiment, includes an elongated member having a length extending from a distal end to a proximal end, and the elongated member having a first lumen and a second lumen. The medical device further includes a first tube and a second tube extending through the first lumen and the second lumen, respectively, from the proximal end of the elongated member to the distal end of the elongated member. An expandable member is fluidly coupled to a distal portion of each of the first tube and the second tube. The first tube, the second tube, and the expandable member are axially movable relative to the elongated member, and the expandable member is configured for deployment between a collapsed configuration and an expanded configuration.

20 Claims, 6 Drawing Sheets

MEDICAL IMMOBILIZATION DEVICE AND RELATED METHODS OF USE

This application claims the benefit of priority from U.S. Provisional Application No. 61/313,040, filed Mar. 11, 2010, which is herein incorporated by reference in its entirety.

FIELD OF THE INVENTION

This invention relates generally to medical devices and methods for retrieving objects within anatomical lumens of the body. More particularly, the invention relates to methods and devices for retrieving and preventing undesired migration of material, such as urinary stones, gall stones, and other objects within anatomical lumens of the body, during a medical procedure.

BACKGROUND OF THE INVENTION

Minimally invasive medical procedures can be used to dispose of problematic concretions that can develop in certain parts of the body, such as in the kidneys, pancreas, and gallbladder. Lithotripsy and ureteroscopy, for example, may be used to treat urinary calculi (e.g., kidney stones) in the ureter of patients. Lithotripsy is a medical procedure that uses energy in various forms, such as acoustic shock waves, pneumatic pulsation, electrical hydraulic shock waves, or laser beams to break up biological concretions such as urinary calculi (e.g., kidney stones). The force of the energy, when applied either extracorporeally or intracorporeally, usually in focused and continuous or successive bursts, divides a kidney stone into smaller fragments that may be extracted from the body or allowed to pass through urination.

Typically, a medical retrieval device, such as a surgical grasper or a metal wire basket, is used to capture a kidney stone in a retrieval assembly during a lithotripsy procedure. With the kidney stone held in position within the retrieval assembly, a lithotriptor, such as a laser lithotriptor, comes within the stone's proximity and fragments it. After the kidney stone is fragmented, the stone fragments can be removed by the same or a different medical retrieval device, or the fragments can be left in the body to be eliminated naturally.

In certain instances, intracorporeal fragmentation of urinary calculi can prove problematic in that stones and/or stone fragments in the ureter may become repositioned closer to and possibly migrate back toward the kidney, thereby requiring further medical intervention to prevent the aggravation of the patient's condition. In these circumstances, the same device or a different medical device may be deployed to control migration and aid in retrieval of fragmented stones. For example, an immobilization device may be deployed within a patient's body, independently or through the working channel of an endoscope, to act as a backstop to prevent upward migration of fragments resulting from a lithotripsy procedure.

These devices, while effective, have certain drawbacks. As physicians sometimes use different instruments to insert the medical retrieval device, lithotripter, and/or immobilization device into a patient's body, the exchange of instruments can cause trauma to the lining of a patient's ureter. Similarly, the exchange of medical devices such as, for example, a lithotripor and an immobilization and/or retrieval device, through a single working channel of, for example, an ureterscope, can prolong the duration of the surgical procedure. Consequently, it may be desirable to have an integrated assembly for preventing migration of stones and fragments, performing the lithotripsy procedure, and extracting residual fragments using a single device, so as to prevent the need for successive instrumentation.

Further, known medical devices for preventing migration of stones and fragments are often made of materials formed at least partially of metals and shape-memory materials such as stainless steel, nitinol, copper, cobalt, vanadium, chromium, iron or the like. The continued deployment, repositioning, and movement of these metallic materials can often cause undesired irritation and unnecessary trauma. Thus, it may be desirable to have alternative methods and devices for preventing upward migration of fragments, while limiting trauma to the patients.

SUMMARY OF THE INVENTION

Embodiments of the present invention are directed to medical devices for immobilization and/or retrieval of objects within anatomical lumens of the body that obviate one or more of the limitations and disadvantages of prior devices.

In one embodiment, the medical device includes an elongated member having a length extending from a distal end to a proximal end, and the elongated member having a first lumen and a second lumen. The medical device further includes a first tube and a second tube extending through the first lumen and the second lumen, respectively, from the proximal end of the elongated member to the distal end of the elongated member. An expandable member is fluidly coupled to a distal portion of each of the first tube and the second tube. The first tube, second tube, and expandable member are axially movable relative to the elongated member, and the expandable member is configured for deployment between a collapsed configuration and an expanded configuration.

In various embodiments, the medical device may include one or more of the following additional features: wherein the first tube is configured to inflate the expandable member for deployment from the collapsed configuration to the expanded configuration; wherein the expandable member is a balloon; wherein the elongated member includes a working channel disposed therein for removably receiving a medical instrument; further including an optical device disposed on or in the elongated member near the distal end of the elongated member; further including a laser fiber received in a third lumen of the elongated member for delivering laser energy through the lumen and beyond the distal end of the elongated member; further comprising a handle at a proximal end of the elongated member, the handle having an actuation mechanism to advance the expandable member from an undeployed position adjacent the distal end of the elongated member to a deployed position distally of the distal end of the elongated member; wherein the elongated member includes a plurality of steering wires connected to the distal end of the elongated member, the steering wires being configured to bend the distal end of the elongated member.

Another embodiment of the invention is directed to a medical device including a handle and an elongated member joined to the handle, the elongated member having a first lumen and a second lumen. The medical device further includes a first tube slidably disposed in the first lumen and a second tube slidably disposed in the second lumen, the first tube and the second tube extending proximally of the handle for connection to a source of fluid. The medical device also includes an expandable member coupled to a distal portion of the first tube and the second tube, the expandable member being axially movable relative to the elongated member, and configured for deployment between a collapsed configuration and an expanded configuration.

In various embodiments, the medical device may include one or more of the following additional features: wherein the handle includes a first actuator and a second actuator, the first actuator being configured to bend the distal end of the elongated member, and the second actuator being configured to advance the expandable member from an undeployed position adjacent the distal end of the elongated member to a deployed position distally of the distal end of the elongated member; further including an optical device disposed on or in the elongated member near the distal end of the elongated member; wherein the expandable member is a balloon; wherein the elongated member further includes a working channel for removably receiving a medical instrument; further including a laser fiber disposed within a third lumen of the elongated member for delivering laser energy through the third lumen and beyond a distal end of the elongated member.

A further embodiment of the invention is directed to a method of immobilizing material in a body. The method includes inserting a medical device into an anatomical lumen of the body. The medical device includes an elongated member having a length extending from a distal end to a proximal end, the elongated member having a first lumen and a second lumen. The medical device further includes a first tube and a second tube extending through the first lumen and the second lumen, respectively, from the proximal end of the elongated member to the distal end of the elongated member. An expandable member is fluidly coupled to a distal portion of each of the first tube and the second tube. The first tube, second tube, and expandable member are axially movable relative to the elongated member, and the expandable member is configured for deployment between a collapsed configuration and an expanded configuration. The method further includes extending the expandable member of the medical device relative to the distal end of the elongated member and beyond the material to be immobilized, and inflating the expandable member so that the expandable member is expanded to the expanded configuration and at least partially occludes the anatomical lumen.

In various embodiments, the method may include: further comprising positioning the elongated member at a treatment site by manipulating a plurality of steering wires connected to the distal end of the elongated member; after inflating the expandable member, delivering laser energy through at least one lumen of the elongated member and beyond the distal end of the elongated member to fragment a stone; during the step of inflating the expandable member, delivering fluid through the first tube and purging air through the second tube; wherein extending the expandable member includes extending expandable member from a position adjacent the distal end of the elongated member to a position distally from the distal end of the elongated member; and retracting the medical device to sweep the anatomical lumen with the expandable member.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Whenever possible, the same reference numbers will be used throughout the drawings to refer to the same or like parts.

Figure 1:
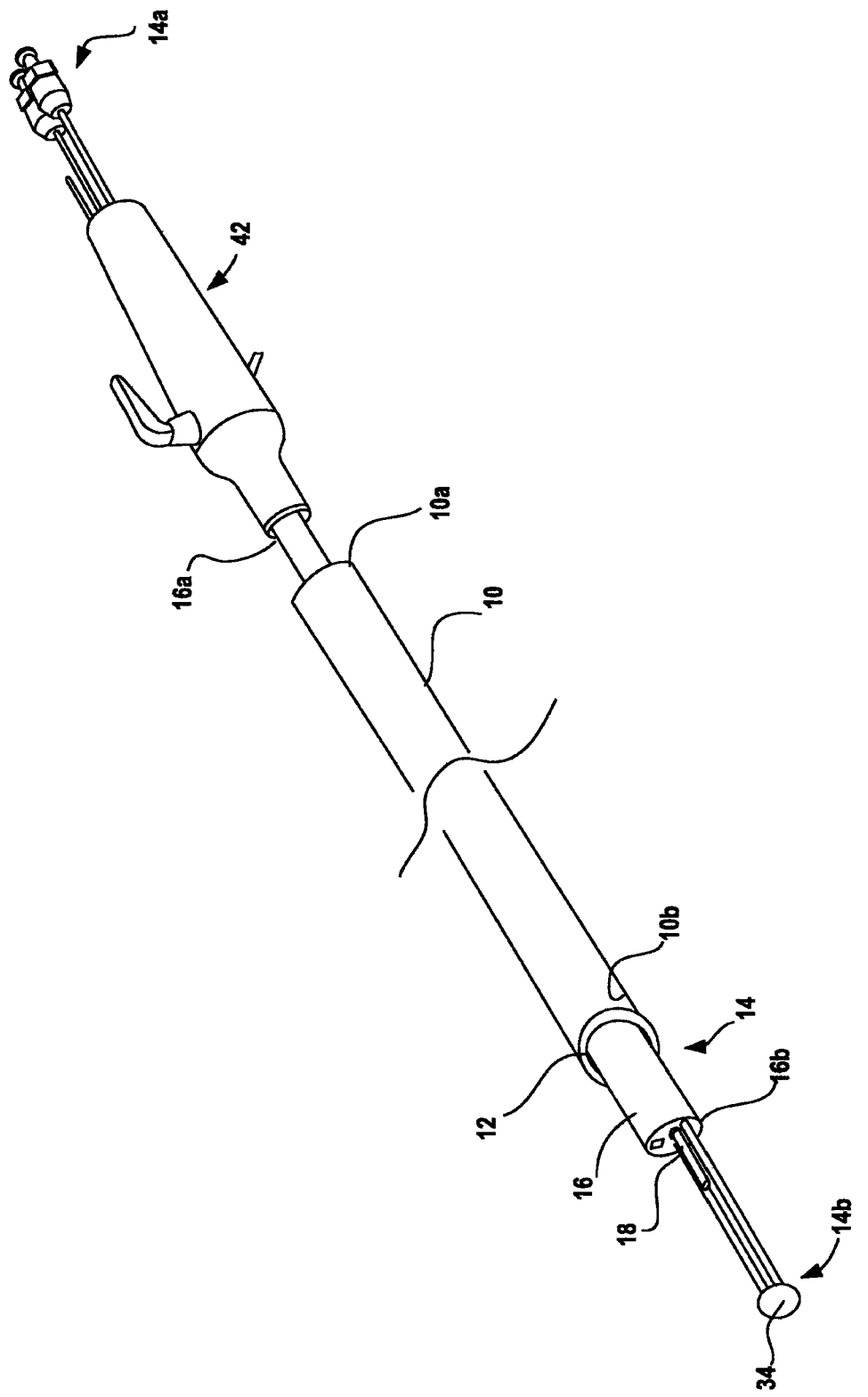
FIG. 1 illustrates a medical device extending through a distal portion of a sheath, according to an embodiment of the invention.

FIG. 1 illustrates a sheath 10 having a proximal portion 10a and a distal portion 10b. For purposes of this disclosure, "distal" refers to the end further from the device operator during use, and "proximal" refers to the end closer to the device operator during use. Sheath 10 may be fabricated by any known process such as, for example, extrusion. In addition, sheath 10 may be made from any suitable material. Such materials may include, but are not limited to, Teflon®, polyimide, and/or stainless steel. Sheath 10 may have any desired cross-sectional shape and/or configuration. For example, sheath 10 may have a substantially circular cross-section. Sheath 10 may also have one or more cross-sectional shapes and/or configurations along its length, and may be any desired dimension suitable for deployment within a desired anatomical lumen. For example, sheath 10 may have dimensions adapted for placement in the human urinary tract having a particular size. The overall length and diameter of the sheath 10 may vary depending on application. For example, a relatively long sheath 10 may be advantageous for retrieving stones or other objects deep within the body of a patient. Furthermore, sheath 10 may also be flexible along at least a portion of its length so that it may conform to the contours of an existing anatomical tract or lumen. Sheath 10 may include at least one lumen 12 extending therethrough for delivering, or removing, for example, a medical device 14 to or from a treatment site.

Medical device 14 may have a proximal portion 14a and a distal portion 14b, and may include an assembly of multiple components including an elongated member 16, a laser fiber 18, and an expandable member 34.

Figure 2:
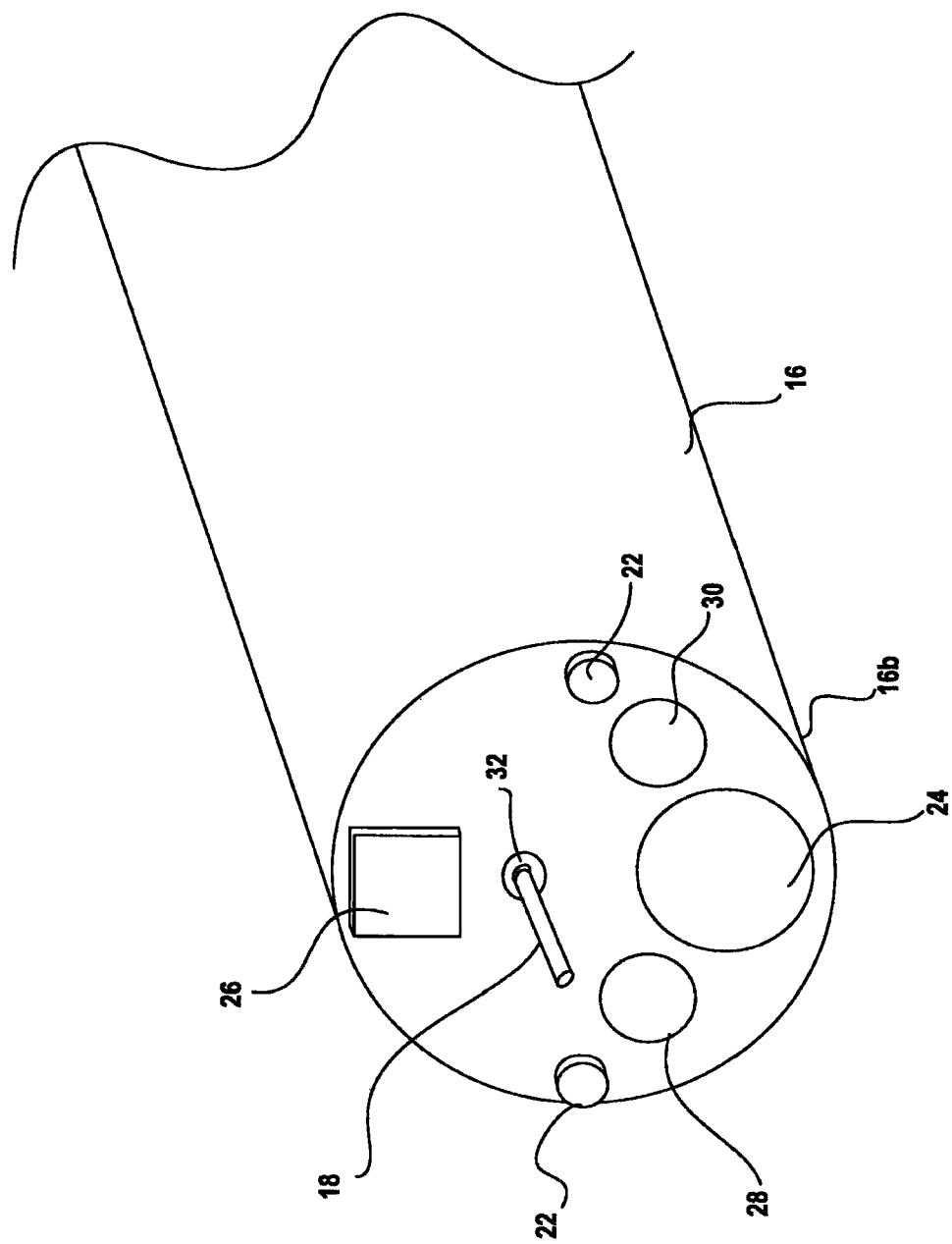
FIG. 2 is a partial perspective view of a distal end of an elongated member of the medical device, according to an embodiment of the invention.

As shown in FIG. 1, elongated member 16 may include a proximal end 16a and a distal end 16b, and may be rigid, malleable, or flexible. Member is preferably flexible for applications within the urinary tract. Elongated member 16 may have any desired cross-sectional shape and/or configuration and may be any desired dimension that can be received within a sheath for entry into an anatomical lumen. Referring to FIG. 2, a plurality of steering wires 22 or other devices may be embedded in elongated member 16 and connected to distal end 16b of elongated member 16 to allow an operator to control movement of elongated member 16 within an anatomical lumen when distal end 16b of elongated member 16 extends beyond distal portion 10b of sheath 10. For example, elongated member 16 may include two steering wires 22 secured to distal end 16b of elongated member 16. Each steering wire 22 extends within a lumen of elongated member 16 from proximal end 16a to distal end 16b. During use, tension may be applied to steering wires 22 to bend distal end 16b of elongated member 16 in one or more directions.

An optic device 26 may be embedded into elongated member 16 at or near distal end 16b of elongated member 16. For example optic device 26 may be mounted on the distal face of elongated member 16. Optic device 26 may include an illumination component, and a camera, lens, digital imaging chip, or other image receiving device, which may transmit (e.g., wirelessly, or using wires or fiber optics embedded along the length of elongated member 16) an image or other signal to a signal processing device, a recorder, or a monitor or other display device viewable by the surgeon.

Elongated member 16 may further include a working channel 24 located therein extending from an access port (not shown) at proximal end 16a of the elongated member to an exit aperture at distal end 16b of the elongated member 16. Working channel 24 may have any suitable size, cross-sectional area, shape, and/or configuration, and may be configured to removably receive a medical instrument 52 (shown in FIG. 8) such as, for example, a basket, grasping forceps, a snare, a needle or any other instrument for performing an operation in a body that may be suitable for urological, endoscopic, or other like procedures. Alternatively, working channel 24 may be an irrigation channel. Although the elongated member 16 shown in FIG. 2 includes a single working channel extending through elongated member 16, one or more additional working channels (not shown) extending through distal end 16b and proximal end 16a of elongated member 16 may be included to provide greater access to the treatment site and/or to receive one or more additional medical instruments for use during the procedure.

Elongated member 16 may additionally have one or more lumens, separate from working channel 24, extending longitudinally therein. In one embodiment, elongated member 16 may include a first lumen 28, a second lumen 30, and a third lumen 32. Although the depicted embodiment of elongated member 16 includes three additional lumens, elongated member 16 may include a greater or lesser number of lumens. Lumens may have any size, cross-sectional area, shape, and/or configuration, and may extend through proximal end 16a and distal end 16b of elongated member 16. For example, first lumen 28, second lumen 30, and third lumen 32 may each have a substantially circular shape with first lumen 28 and second lumen 30 having a larger cross-sectional area than third lumen 32. It is contemplated that, in addition to first lumen 28, second lumen 30, and third lumen 32, an aspiration lumen and/or an irrigation lumen may extend longitudinally through elongated member 16. Alternatively, working channel 24 may be used for irrigation and/or aspiration.

Laser fiber 18 may be disposed within third lumen 32 of the elongated member 16, and movable relative to elongated member 16 so that laser fiber 18 extends beyond distal end 16b of elongated member 16. Laser fiber 18 may be any conventional laser used in lithotripsy procedures such as, for example, Holmium lasers, NDYAG lasers, $CO_2$ dialed lasers, and/or Candella lasers. Laser fiber 18 may be configured to deliver laser energy through third lumen 32 and beyond distal end 16b of elongated member 16 to fragment biological concretions such as urinary calculi (e.g., kidney stones).

Figure 3A:
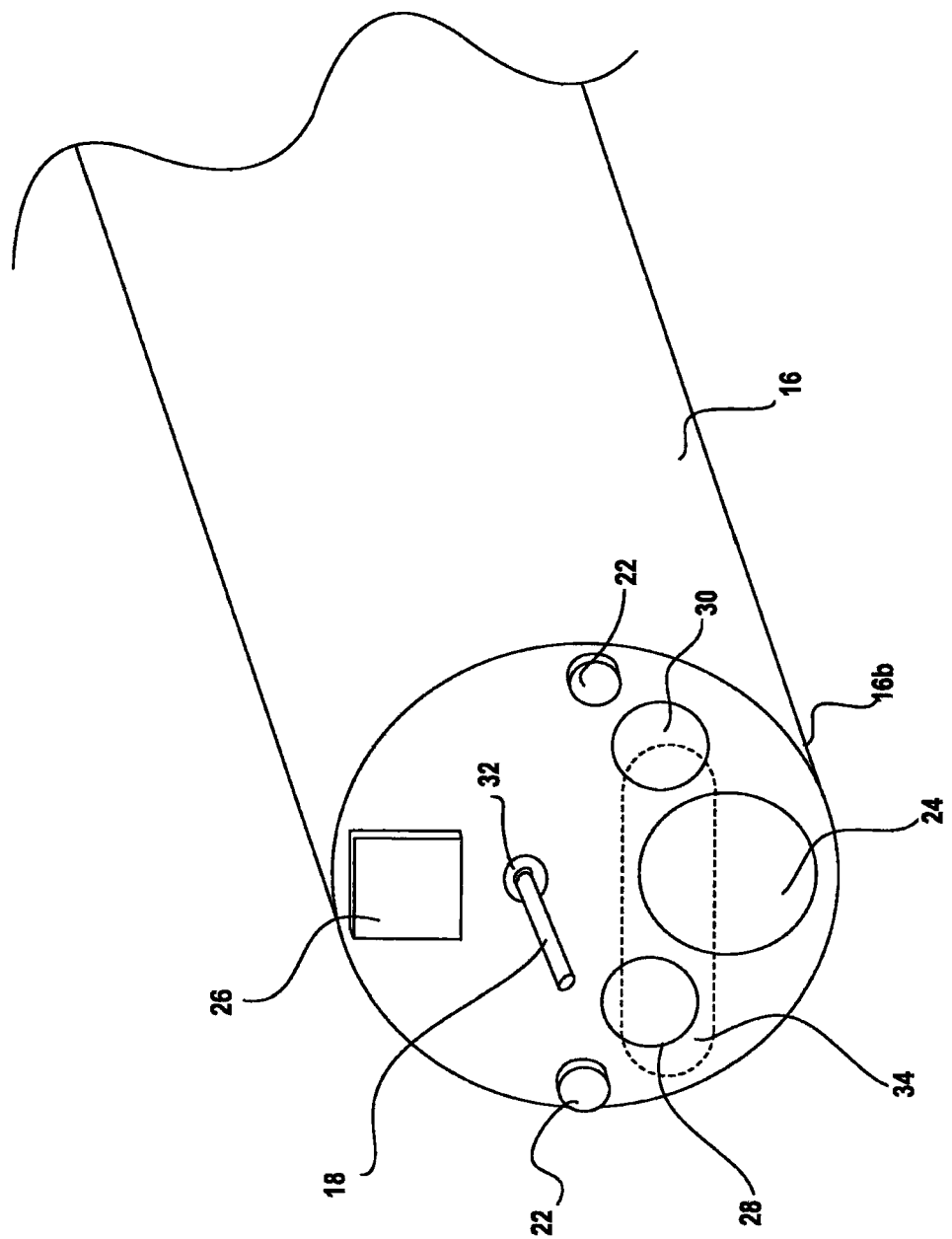
FIG. 3A is a partial perspective view of an expandable member of the medical device in an undeployed position, according to an embodiment of the invention.
Figure 3B:
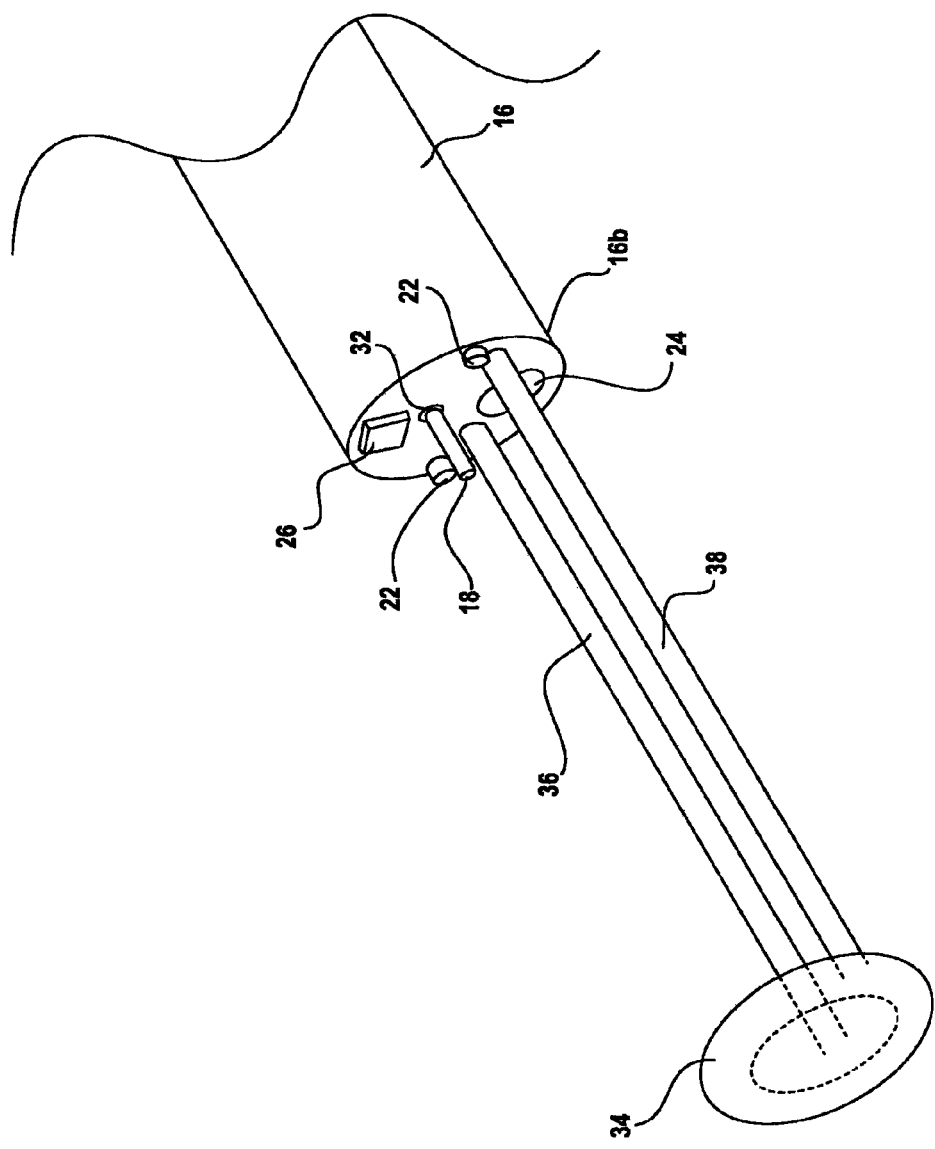
FIG. 3B is a partial perspective view of the expandable member of FIG. 3A in a deployed position according to an embodiment of the invention.

Referring now to FIGS. 3A and 3B, an immobilization device including an expandable member 34, a first tube 36, and a second tube 38 may be positioned adjacent to distal end 16b of elongated member 16. Expandable member 34 may be fluidly connected to first tube 36 which extends proximally through first lumen 28 of elongated member 16, and second tube 38 which extends proximally through second lumen 30 of elongated member 16. First tube 36 and second tube 38 may be movable relative to elongated member 16 in order to advance expandable member 34 from an undeployed position adjacent to distal end 16b of elongated member 16 (FIG. 3A) to a deployed position distally of distal end 16b of elongated member 16 (FIG. 3B).

First tube 36 and second tube 38 may be spaced apart and interconnected by expansible member 34. First tube 36 may be fluidly connected to expansible member 34 at a position that is diametrically opposed to second tube 38, so as to radially expand expandable member 34 in the undeployed position. First tube 36 and second tube 38 may also be positioned below laser fiber 18 to facilitate free movement of laser fiber 18. In the deployed position, first tube 36 and second tube 38 may be offset from a longitudinal axis of elongated member 16 and extend from either side of working channel 24 to facilitate free movement of, for example, a medical instrument extending through working channel 24, and provide a larger working space at the treatment site.

First tube 36 and second tube 38 may be fabricated by any known process such as, for example, extrusion. In addition, first tube 36 and second tube 38 may be made from any suitable material. First tube 36 and second tube 38 may have any cross-sectional area, shape, and/or configuration. The overall length of first tube 36 and second tube 38 may vary depending on application. For example, a lengthy first tube 36 and second tube 38 may be advantageous to define a larger working space within an anatomical lumen in which the lithotripsy procedure may occur.

In some embodiments, medical device 14 may include a single tube extending proximally through elongated member 16 to facilitate the free movement of an associated laser fiber (or any other instrument required by the procedure) by allowing a less congested internal working area at the desired treatment site.

Figure 4:
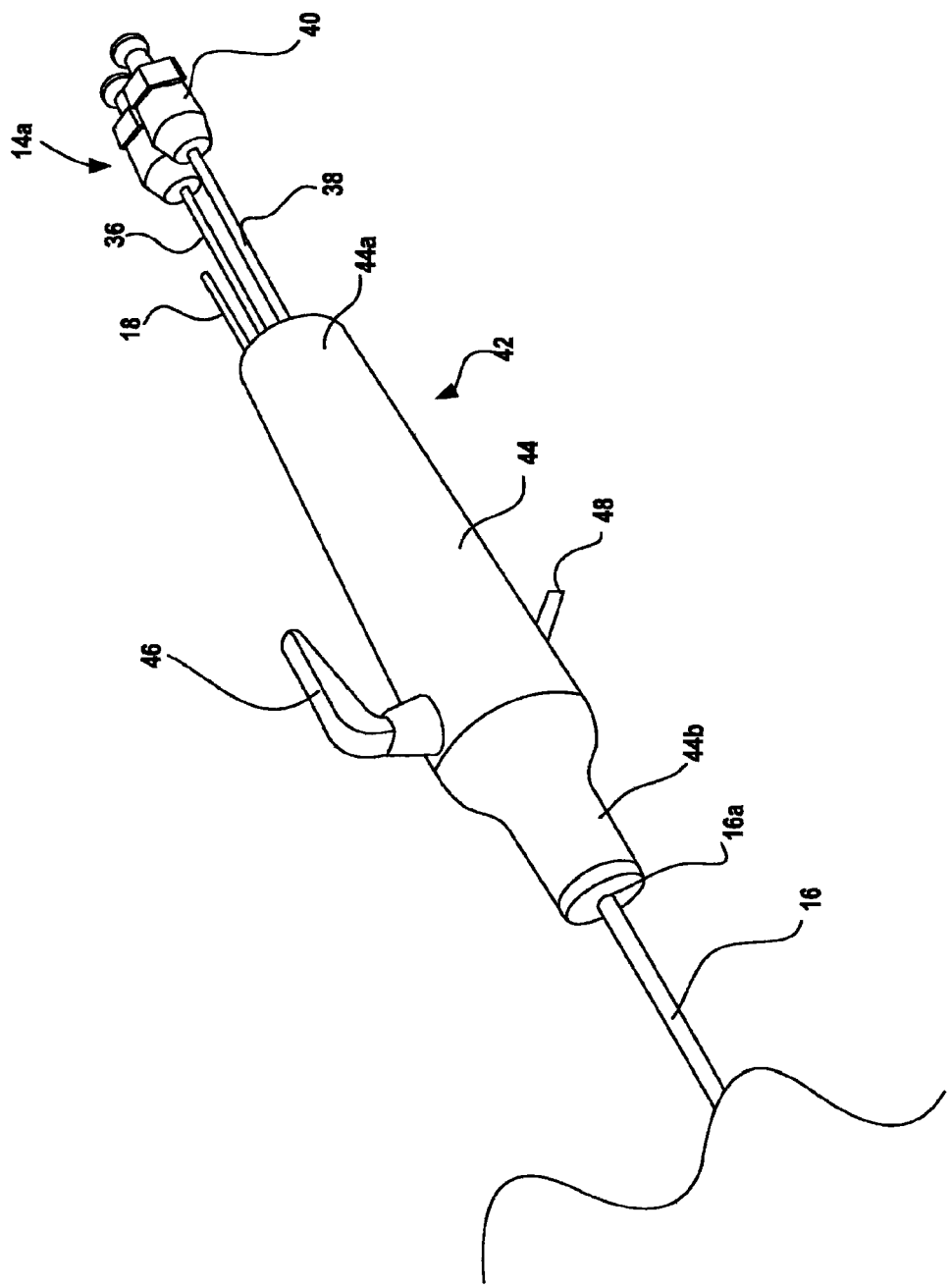
FIG. 4 partial perspective view of a proximal portion of the medical device, according to an embodiment of the invention.

First tube 36 and second tube 38 each may define a lumen (not shown) extending longitudinally therein through which a fluid, such as a liquid or gas, may pass to expand (inflate) and contract or collapse (deflate) the expandable member 34. For example, the inflation fluid may be air, water, carbon dioxide, or saline solution. As shown in FIG. 4, each of first tube 36 and second tube 38 may be fluidly connected at one end to a luer fitting 40 and at an opposite end to the expandable member 34. Luer fitting 40 may be configured to permit fluid to enter its corresponding first tube 36 or second tube 38, and may also allow the surgeon to vent fluid from inside expandable member 34 through the other of first tube 36 and second tube 38.

For example, a source of the inflation fluid, such as a pump or syringe, may be connected to the luer fitting 40 to direct inflation fluid into one of first tube 36, second tube 38, and expandable member 34. After expandable member 34 is expanded to a desired expanded configuration, the source of the inflation fluid may be disconnected from luer fitting 40, and then luer fitting 40 may prevent the inflation fluid from exiting first tube 36, second tube 38, and expandable member 34. In some embodiments, a source of suction, such as a syringe, may also be connected to luer fitting 40 to remove air from the expandable member 34 as inflation fluid is used to inflate and expand expandable member 34.

The phrase "expandable member" generally relates to any expandable structure, such as a balloon or other inflatable structure, regardless of the elasticity of the material comprising the structure. For example, the phrase "expandable member" may denote a thin-walled structure made of material of low elasticity (which does not stretch significantly during inflation) or highly elastic material (which does stretch significantly during inflation). For example, expandable member 34 may be made from polyethylene terephthalate (PET), polyurethanes, polyethylenes and ionomers, copolyesters, rubbers, polyamides, silicone, latex, or any other suitable materials known in the art. Expandable member 34 may be mechanically, electrically, pneumatically or hydraulically expanded and collapsed without departing from the scope of the invention.

FIG. 3A shows an exemplary embodiment of expandable member 34 in an collapsed configuration, and FIG. 3B shows the expandable member 34 in an expanded configuration. The particular expanded exterior configuration of expandable member 34, such as the volume, width, depth, radius, length, or other dimension, may be selected so that expandable member 34 substantially occludes an anatomical lumen in the expanded configuration. For example, in the embodiments shown in FIG. 3B, the expandable member 34 in its expanded configuration may be spherical in shape. It is understood that the outer profile of expandable member 34 may have an oval, elliptical, square, rectangular or any other shape known to one skilled in the art.

Referring now to FIG. 4, proximal end 16a of elongated member 16 extends into handle 42. Handle 42 may include an elongated handle body 44 having a thumb lever 46 and an actuation mechanism 48 disposed on handle 42.

Thumb lever 46 may be located closer to a distal end 44b than a proximal end 44a of the handle 42, and may be operatively connected to steering wires 22 embedded in elongated member 16. Thumb lever 46 may be configured to pivot relative to handle body 44 to control movement of distal end 16b of elongate member 16. Actuation mechanism 48 may be disposed on handle 42 proximate thumb lever 46 so that an operator may grip handle 42 with a single hand to rotate thumb lever 46 with an operator's thumb and actuate actuation mechanism 48 with another finger of the same hand.

Actuation mechanism 48 may be operatively connected to first tube 36 and second tube 38 to advance expandable member 34 from an undeployed position to a deployed position. In one embodiment, actuation mechanism 48 may include a trigger. Alternatively, actuation mechanism 48 may be a slide actuator, a button, or any other actuation mechanism 48 known to one skilled in the art for controlled deployment of expandable member 34.

In an alternative embodiment, handle 42 may only include thumb lever 46, and expandable member 34 may be manually extended from an undeployed position to a deployed position. In yet another alternative embodiment, a second actuation mechanism may be disposed on handle 42 and connected to the laser fiber 18 to selectively advance laser fiber 18 from and/or retract laser fiber 18 into elongated member 16.

Figure 5:
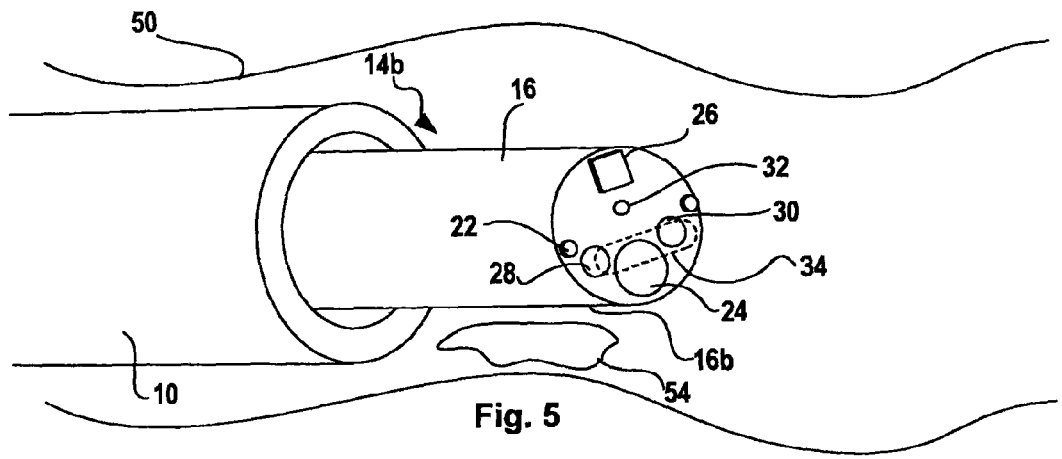
FIG. 5 illustrates a distal portion of the medical device deployed beyond a kidney stone in a ureter, according to an embodiment of the invention.
Figure 6:
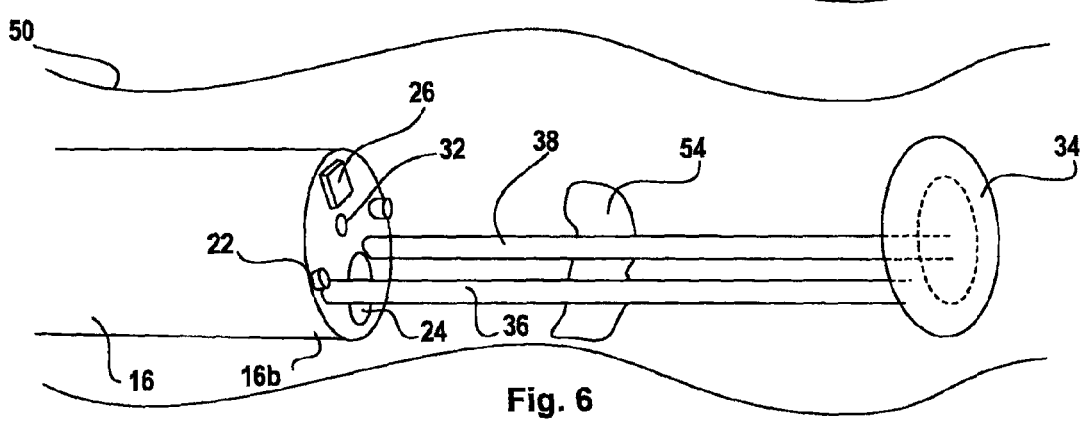
FIG. 6 illustrates the medical device having an expandable member deployed beyond the kidney stone in the ureter and a laser fiber positioned proximate to the kidney stone, according to an embodiment of the invention.

FIGS. 5-8 illustrate systems and methods for retrieving, immobilizing, and/or preventing migration of objects in anatomical lumens during a medical procedure. Referring to FIG. 5, medical device 14 may be advanced through a sheath 10 to be positioned at an internal treatment site in an anatomical lumen, for example, such as within a patient's ureter 50. To facilitate insertion, sheath 10 may include radiopaque marker bands (not shown) detectable by x-ray or other imaging means. Alternatively, medical device 14 may be fed to the treatment site without sheath 10. For example, in some embodiments, medical device 14 may include a tapered tip for insertion into the body.

A distal end 14b of medical device 14 may be positioned distally beyond a biological concretion such as urinary calculi (e.g., a kidney stone 54), for example. To facilitate positioning of medical device 14 and navigation of ureter 50, an operator may manipulate steering wires 22 embedded in elongated member 16 of medical device 14 to point distal end 16b of elongated member 16 of medical device 14 in a desired direction. The operator may additionally visualize the treatment site and/or stone through optical device 26 provided on distal end 16b of elongated member 16.

Once positioned, expandable member 34 may be advanced distally from an undeployed position adjacent to distal end 16b of elongated member 16 to a deployed position (FIG. 6) distally to distal end 16b of elongated member 16. This may be achieved by actuating actuator mechanism 48 of handle 42. In the deployed position, inflation fluid may be delivered through one of first tube 36 and second tube 38 to the expandable member 34 to inflate the expandable member 34 from a collapsed configuration to an expanded configuration having a desired size, shape and/or pressure to partially or completely occlude ureter 50. Air may be purged from expandable member 50 through the other of first tube 36 and second tube 38 during the inflation of expandable member 34 to facilitate expansion of expandable member 34. In some embodiments, delivery of inflation fluid may be modulated to control the pressure of expandable member 34 on walls of ureter 50.

Once expandable member is deployed, distal end 16b of elongated member 16 may be deflected by manipulating steering wires 22. In this manner, medical device 14 and, more particularly, expandable member 34, may be capable of achieving a variety of positions within ureter 50.

Figure 7:
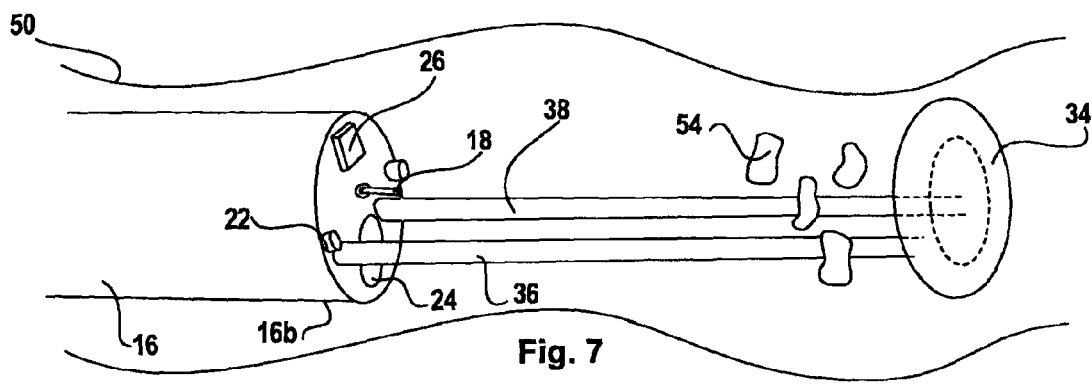
FIG. 7 illustrates retrieval of the kidney stone after fragmentation, according to an embodiment of the invention.

Depending on the size of the targeted stone 54, expandable member 34 can be used as a tool to move stone 54 proximally along ureter 50. In the expanded configuration, medical device 14 can be moved proximally along the ureter 50 to sweep stone 54 in the proximal direction. Upon the continued proximal movement of medical device 14, stone 54 may be swept and repositioned to a new location more accessible for retrieval and removal, or swept from the ureter 50 altogether. Additionally and/or alternatively, a medical instrument 52 such as, for example, a grasping forceps, may be inserted through working channel and introduced in into anatomical lumen 50 to reposition or remove the stone 54.

Where a concretion, such as kidney stone 54, is too large to be extracted without fragmentation, a laser fiber 18 can be advanced through third lumen 32 of elongated member 16 for directing laser energy at kidney stone 54 in order to break down the concretion into smaller pieces to facilitate retrieval or normal passage through the bladder (FIG. 7).

Figure 8:
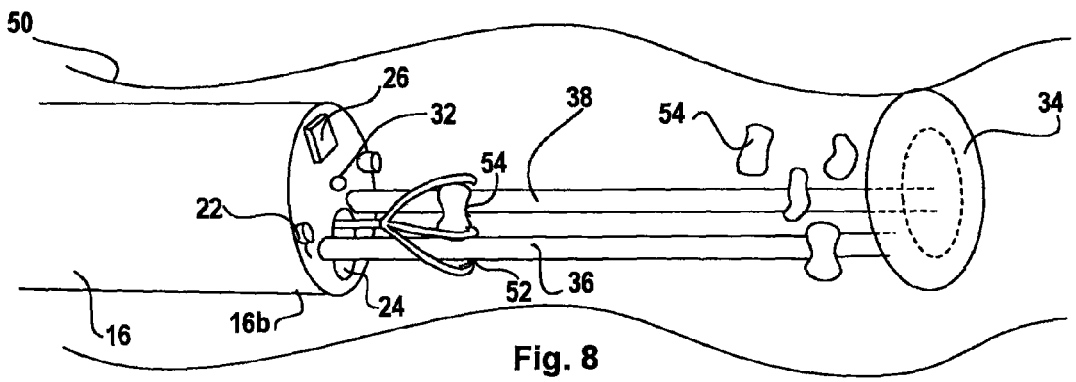
FIG. 8 illustrates a medical instrument introduced through the elongated member to retrieve or reposition the kidney stone, according to an embodiment of the invention.

After a lithotripsy procedure is completed, kidney stone 54 is fragmented into multiple smaller stones. During the lithotripsy procedure, expandable member 34 serves as a backstop to prevent migration of the smaller stones, thereby preventing complications resulting from the potential migration of stones back into, for example, a patient's kidneys. After the fragmentation of stone 54, laser fiber 18 is withdrawn and the expandable member 34 can then be pulled proximally along ureter 50 to sweep the remaining smaller stones toward, for example, the bladder to be voided or repositioned to facilitate retrieval by an additional medical instrument 52 (FIG. 8). For example, a grasping forceps may be inserted through working channel 24 and introduced in into anatomical lumen 50 to reposition or remove the stone.

With the aid of optical device 26, the operator of medical device 14 can monitor the progress of the lithotripsy procedure and terminate treatment when residual fragments are small enough to be voided or removed.

One advantage of the embodiment of medical device 14, illustrated in FIGS. 5-8, is that expandable member 34, laser fiber 18, optical device 26, and/or a medical instrument 52 such as, for example, a grasper, are provided in an integrated medical device 14. As noted above, in the past devices where a backstop was deployed distally beyond a kidney stone, the backstop was either provided through the same working channel that received the lithotriptor and/or retrieval device, or independently of those devices. As a result, the working area at the treatment site would be congested and would obstruct the free movement of any one of the devices. Moreover, where the backstop was provided through the same working channel that received the lithotripter and/or retrieval device, repeated insertion and removal of the devices were required, causing trauma to the patients and prolonging the duration of the procedure.

Medical device 14, in contrast, provides an integrated medical device to fragment concretions, immobilize fragments, and visualize the treatment site, thereby providing improved simplicity for the operator and ease of use. Additionally, medical device provides improved efficiency as fewer insertions are required. As a result, safer treatment procedures and shorter treatment durations are realized.

While this specification makes reference to endoscope devices, the invention is not intended to be so limited. Accordingly, the elements described in this application may be used with any other medical device requiring, or even benefiting from, an immobilization/retrieval assembly. Other embodiments of the invention will be apparent to those skilled in the art from consideration of the specification and practice of the invention disclosed herein. It is intended that the specification and examples be considered as exemplary only.

What is claimed:

1. A medical device comprising:
   an elongated member having a length extending from a distal end to a proximal end, the elongated member having a first lumen and a second lumen;
   a first tube extending through the first lumen from the proximal end of the elongated member to the distal end of the elongated member;
   a second tube extending through the second lumen from the proximal end of the elongated member to the distal end of the elongated member; and
   an expandable member fluidly coupled to a distal portion of both of the first tube and the second tube, the first tube, the second tube, and the expandable member being axially movable relative to the elongated member, wherein the expandable member is configured for deployment between a collapsed configuration and an expanded configuration.

2. The medical device of claim 1, wherein the first tube is configured to inflate the expandable member for deployment from the collapsed configuration to the expanded configuration.

3. The medical device of claim 1, wherein the expandable member is a balloon.

4. The medical device of claim 1, wherein the elongated member includes a working channel disposed therein for removably receiving a medical instrument.

5. The medical device of claim 1, further including an optical device disposed on or in the elongated member near the distal end of the elongated member.

6. The medical device of claim 1, further including a laser fiber received in a third lumen of the elongated member for delivering laser energy through the third lumen and beyond the distal end of the elongated member.

7. The medical device of claim 1, further comprising a handle at a proximal end of the elongated member, the handle having an actuation mechanism to advance the expandable member from an undeployed position adjacent the distal end of the elongated member to a deployed position distally of the distal end of the elongated member.

8. The medical device of claim 1, wherein the elongated member includes a plurality of steering wires connected to the distal end of the elongated member, the steering wires being configured to bend the distal end of the elongated member.

9. The medical device of claim 7, wherein the first tube and the second tube extend proximally of the handle for connection to a source of fluid.

10. The medical device of claim 9, wherein the handle includes a first actuator and a second actuator, the first actuator being configured to bend the distal end of the elongated member, and the second actuator being configured to advance the expandable member from an undeployed position adjacent the distal end of the elongated member to a deployed position distally of the distal end of the elongated member.

11. The medical device of claim 9, further including an optical device disposed on or in the elongated member near the distal end of the elongated member.

12. The medical device of claim 9, wherein the expandable member is a balloon.

13. The medical device of claim 9, wherein the elongated member further includes a working channel for removably receiving a medical instrument.

14. The medical device of claim 9, further including a laser fiber disposed within a third lumen of the elongated member for delivering laser energy through the third lumen and beyond the distal end of the elongated member.

15. A medical device comprising:
    an elongated member having a length extending from a distal end to a proximal end, the elongated member having a first lumen and a second lumen;
    a first tube extending through the first lumen from the proximal end of the elongated member to the distal end of the elongated member;
    a second tube extending through the second lumen from the proximal end of the elongated member to the distal end of the elongated member; and
    an expandable member fluidly coupled to a distal portion of both of the first tube and the second tube, wherein the first tube and second tube are spaced apart and interconnected by the expandable member.

16. The medical device of claim 15, further comprising a laser fiber received in a third lumen of the elongated member for delivering laser energy through the third lumen and beyond the distal end of the elongated member.

17. The medical device of claim 16, wherein the first and second tubes are positioned below the laser fiber.

18. A medical device comprising:
an elongated member having a length extending from a distal end to a proximal end, the elongated member having a first lumen and a second lumen;
a first tube extending through the first lumen from the proximal end of the elongated member to the distal end of the elongated member;
a second tube extending through the second lumen from the proximal end of the elongated member to the distal end of the elongated member; and
an expandable member fluidly coupled to a distal portion of both of the first tube and the second tube, the first tube, the second tube, and the expandable member being axially movable relative to the elongated member,
wherein:
the expandable member is configured to transition between a collapsed configuration and an expanded configuration, and
one of the first tube or second tube is configured to expand the expandable member and the other of the first tube or second tube is configured to collapse the expandable member.

19. The medical device of claim 18, wherein the expandable member is a balloon.

20. The medical device of claim 18, wherein the elongated member includes a working channel disposed therein for receiving a medical instrument.

\* \* \* \* \*